United States Patent [19]

Gibson

[11] Patent Number: 4,992,296

[45] Date of Patent: Feb. 12, 1991

[54] ABUSE-TYPE DRUG TEST PAPERS AND METHODS OF MAKING AND USING SAME

[76] Inventor: Jacob J. Gibson, 36 Bonner Dr., Glens Falls, N.Y. 12804

[21] Appl. No.: 316,334

[22] Filed: Feb. 24, 1989

Related U.S. Application Data

[63] Continuation-in-part of Ser. No. 54,199, May 26, 1987, abandoned, which is a continuation-in-part of Ser. No. 808,378, Dec. 16, 1985, abandoned, which is a continuation of Ser. No. 520,463, Aug. 4, 1983, abandoned.

[51] Int. Cl.$^5$ .................. A61K 9/70; G01N 21/78; G01N 33/52
[52] U.S. Cl. ........................... 427/2; 422/56; 422/57; 422/58; 436/92; 436/96; 436/98; 436/111; 436/169; 436/901; 436/39; 427/258; 427/377; 427/380; 427/382; 427/439
[58] Field of Search .................. 422/56–58; 436/92, 96, 98, 111, 169, 901, 39; 427/2

[56] References Cited

U.S. PATENT DOCUMENTS 3,912,655  10/1975  Shulka ........................... 422/56
3,915,639  10/1975  Friendenberg ............... 23/230 B

*Primary Examiner*—Robert J. Warden
*Assistant Examiner*—David Redding
*Attorney, Agent, or Firm*—Schmeiser, Morelle & Watts

[57] ABSTRACT

A method of making drug abuse test papers wherein bibulous paper carriers are impregnated with specific test chemicals, (bismuth subnitrate, potassium iodide, acetic acid, and platinum salt), in two coatings and dried after each coating under specific temperature conditions. The test chemicals are provided for the detection of the drug abuse compounds of amphetamine, cocaine, marijuana, and narcotics contained in low concentrations in animal or human urine. Additionally described is a means of preserving urine samples using esters of parahydroxybenzoic acid.

5 Claims, No Drawings

ABUSE-TYPE DRUG TEST PAPERS AND METHODS OF MAKING AND USING SAME

This is a continuation-in-part of U.S. patent application Ser. No. 07/054,199, filed May 26, 1987, which is a continuation-in-part of U.S. patent application Ser. No. 808,378, filed Dec. 16, 1985, now abandoned, which is a continuation of U.S. patent application Ser. No. 520,463, filed Aug. 4, 1983, now abandoned.

TECHNICAL FIELD

This invention relates to a method and means for detecting the presence of certain drugs of abuse, namely amphetamines, cocaine, marijuana and morphine like compounds as a group as well as individual narcotics, specifically methadone and morphine glucorinide in physiological fluids. This invention relates to a combination of chemicals impregnated in a bibulous paper used as a carrier for said test chemicals reactive to indicate the presence of said drug abuse compound residues by use of said test paper.

BACKGROUND OF THE INVENTION

The increase of drug abuse has created a need for new methods of analyzing drug residues in physiological fluids that are accurate, rapid and cost effective. Most methods require large capital expenditures for equipment, are time consuming and are costly per unit test.

U.S. Pat. No. 3,915,639 issued October 1975 to Friedenberg discloses a method for dipstick identification of drugs of abuse based upon the incorporation of an ion-exchange resin in a bibulous support together with a hydrazine salt which acts as a stain intensifying agent. It is found that the preferred hydrazine, 2-4 dinitrophenyl, is not soluble in common solvents and is not functional in the manner disclosed. Applicant here uses neither the hydrazines or ion-exchange resins.

SUMMARY OF THE INVENTION

It is an object of this invention to provide a method and means, such as a chemically treated test paper, for the rapid determination of the above listed drug residues as they might exist in the physiological fluids of drug abusers.

Another object of this invention is to provide a means for rapid identification of particular species of drug residues when present in a concentration of over one microgram per milliliter of the test fluid.

It is a further object of this invention to provide a test paper of such high sensitivity to specific abuse-type drugs in said quantity or range to provide a semi-permanent color as a record of the presence of such drug in the physiological fluid tested.

Still another object of the present invention is to provide a method and means for stabilizing addict's urine so that these urines may be used as biological controls for use with the test paper for an extended period of time without the need for refrigeration.

The term "physiological fluid" refers most commonly to urine.

The drug residues which are usefully identifiable are Amphetamine/broad deep grey band, Cocaine/orange band, Heroin/metabolite is morphine glucorinide - blue ring or band, Marijuana/THC metabolite-charcoal ring and Percodan/tan band. Rehabilitation patient urine will usually reveal Methdone/broad purple band.

The bibulous carrier is a chemically treated test paper which may be of any suitable shape or form and refers to paper, fibers or polymers having the requisite physical properties stated below.

It is found that the following indicators bismuth, usually as the subnitrate, iodide, usually potassium iodide, and various salts of platinum, applied as composite solutions to the test paper under specific physical conditions will yield a quick means for determining the presence of various drug residues in small urine samples.

An occasional addict patient may attempt to substitute water and this is quickly identified because one of the test papers will turn black immediately upon exposure to water instead of urine.

The urine is tested as follows: 0.05 ml is taken up into a capillary tube and this is placed vertically directly in the center of a 1¼ inch square of chemically impregnated test paper. The urine is allowed to diffuse of its own accord into the paper—about 10 seconds. The paper is allowed to dry and can be read within five minutes. Better discrimination from a well defined chromatogram is achieved by introducing 0.1 ml of urine onto the 1¼ inch square of test paper by way of two drops delivered at 5 second intervals in the same locus from a vertically held medicine dropper or pasteur pipet. This is somewhat less sensitive than the first procedure but can be used as an adjunct.

Bibulous Test Paper

Cellulose filter paper will be insensitive if too thin and poor chromatograms will form if the paper is too thick. The paper should have a thickness at least in a range of 0.35 to 0.45 mm. A paper having about 0.4 mm thickness and a dry weight of about 185 g/m² is preferred.

TEST PAPER FORMULATIONS

Where Pt salt is shown in the formulas below, substitute any high quality salt from the group: $K_2PtCl_4$, $K_2PtCl_6$, $H_2PtCl_6$, $PtCl_3$ and $PtCl_4$. The salt is put into solution by trituration in a glass mortar with a glass pestle using fresh saturated potassium iodide. This is then washed into a flask with the water and acid and allowed to age for 48 hours prior to use.

The quality of a Pt salt can be determined by making an iodochloroplatinate test paper as for cocaine without the bismuth addition. A drop of fluid from a spiked urine specimen should reveal a faint grey ring if the concentration of the spike is one microgram per ml of caffeine or morphine sulfate.

Two separate immersion procedures with a curing period of two weeks between the first and second dips are preferred.

Four reagent solutions are required:

| (A) | Bismuth subnitrate | 1.4 | gm |
|---|---|---|---|
|  | Acetic acid, glacial | 14.0 | ml |
|  | Water, qs | 100 | ml |
| Allow 48 hours for complete dissolution. |  |  |  |
| (B) | Potassium iodide | 4.05 | gm |
|  | Pt salt | 0.45 | gm |
|  | Water | 100 | ml |
|  | 2 N Hydrochloric acid | 100 | ml |
| (C) | Potassium iodide | 6.0 | gm |
|  | Pt salt | 0.125 | gm |
|  | Water | 50 | ml |
|  | 2 N Hydrochloric acid | 50 | ml |
| (C) | Alternative |  |  |
|  | Potassium iodide | 7.2 | gm |
|  | Pt salt | 0.15 | gm |
|  | Water | 100 | ml |

|     |                     |          |
| --- | ------------------- | -------- |
|     | 2N Hydrochloric acid | 100 ml   |
| (D) | Potassium iodide    | 1.125 gm |
|     | Pt salt             | 0.125 gm |
|     | Water               | 100 ml   |
|     | 2N Hydrochloric acid | 100 ml   |
| (D) | Alternative         |          |
|     | Potassium iodide    | 1.35 gm  |
|     | Pt salt             | 0.15 gm  |
|     | Water               | 100 ml   |
|     | 2N Hydrochloric acid | 100 ml   |

The first immersion using the (B) solution will receive the (C) solution two weeks later and the first immersion using the (D) solution will receive the (B) solution as a final dip two weeks later.

On day of use the (A)+(B) solutions are each warmed to 40° C. and mixed, the Pt solution is first poured into a 2 liter hand held beaker and swirled while the (A) solution is added slowly into the center of the swirl. The mixed composite reagent is then poured into a warm dish and held at this same temperature during the paper dipping process. This also applies when the (A)+(C) and (A)+(D) solutions are used. The bismuth, (A) solution, will tend to separate out of solution as black flakes if cold solutions are mixed. This may also occur if it is splashed on the sides of the mixing vessel.

Test paper made only from (B)+(D) solutions will show a grey ring for all alkaloids including caffeine. Methadone and water show nothing. When minute amounts of (A) is added to the (B)+(D) solutions we find that the orange band occuring when cocaine is present is enhanced. Test paper made with only the (A) solution is insensitive to all drugs. But on addition of 5% KI, the (A) solution takes on a brilliant yellow color and paper dipped in that solution and then dried will only respond to water, revealing instantaneously a black spot.

EXAMPLE 1—for all drugs in Table 1 but not cocaine.

First Immersion 10 ml of solution (A), prewarmed, is added to 100 ml of warm solution (B). Sheets of the bibulous paper, with splines affixed at one end, are immersed in the composite reagent held in a warm dish. The splines are then suspended from lines in an environmental room maintained at 30° C. for static drying, about 3 hours. The papers are then allowed to cure for two weeks in a holding area. They can be loosely boxed for this same period of time if preferred.

Second Immersion 100 ml of prewarmed solution (A) is added slowly with continuous agitation to 100 ml of solution (C) also prewarmed. The mixed composite reagent is poured into a warm dish and the cured papers from the first dip are now immersed for the second time.

The papers are again suspended in static air in the environmental room. The temperature for this drying cycle is 50° C. High humidity is also required. Drying is complete after 3 hours and the papers can then be cut to size and packed loosely in free air. The papers will remain effective for over six months if they are kept cool.

EXAMPLE 2—a Cocaine Test Paper

First Immersion 1 ml of warm solution (A) is added to 100 ml of warm solution (D) Alternative. All conditions shown for first immersion in Example 1 are followed.

Second Immersion 1 ml of warm solution (A) is added to 100 ml of warm solution (B). All conditions shown for first immersion in Example 1 are followed. These papers will be ready for use upon drying.

Urine specimens will be required for testing or control purposes. This could be an ongoing problem since urine decomposes rapidly unless frozen. I have found that urine can be preserved, so that there is no change of pH or objectionable odor or other evidence of contamination when standing at room temperature for at least six months, by the addition of any ester of parahydroxybenzoic acid from the group comprising, methyl, ethyl, propyl, butyl or benzyl esters. The esters are neutral, inert and present no interference with either the urinary drug or the test papers.

EXAMPLE 3

| | |
| --- | --- |
| Methyl parahydroxybenzoic acid | 8 gm |
| Propyl parahydroxybenzoic acid | 2 gm |
| Acetone | 100 ml |

2.5 ml of the above is mixed with 100 ml of urine and the MPB will be at 0.2% concentration and the PPB will be at 0.05% concentration. The two esters shown are readily available.

EXAMPLE 4

First Immersion (for all drugs except cocaine)

Prewarmed (B) solution is poured into a warm dish and sheets of bibulous paper with splines attached at one end are immersed in the warm reagent. The splines are then suspended from lines in an environmental room where the temperature is maintained at about 30° C. The paper is dry in about 3 hours under static conditions after which they are loosely boxed for a curing period of 1-2 weeks.

Second Immersion

Papers from the first immersion are immersed in a composite reagent of 100 ml of warm solution (A) which has been mixed with 100 ml of warm solution (C) and then suspended in static air in the environmental room at temperature about 50° C., supplemental humidity being provided so that the relative humidity during the first hour is greater than about 90%. The relative humidity will diminish from that level gradually over the next two hours while drying is completed. The supplemental humidity is provided in any suitable manner, as known to those skilled in the art.

EXAMPLE 5

First Immersion

Prewarmed solution (A) in the amount of 5 ml is added to 100 ml of prewarmed solution (B) and papers are immersed in it as described in Example 4. These papers then are dried and subjected to a second immersion, both steps being carried out using the procedure and the solution described in Example 4.

EXAMPLE 6—for cocaine paper

First Immersion

Papers are immersed in warm solution (D) Alternative. These papers then are dried and subjected to a secondary immersion in warm solution (B), both steps being carried out using the drying procedure of the first immersion of Example 4.

TABLE 1

Summary of color reactions with the test papers five minutes after placement of urine.*

| | |
|---|---|
| Water adulterant | instant diffuse black* |
| Normal | buff center, brown or thin purple periphery |
| Non specific normal morphine sulfate SPIKE | inner purple ring |
| Ammoniacal | green-grey ring inward of the periphery |
| Caffeine/Nicotine | thin grey band against the periphery |
| Amphetamine | very broad deep grey band against periphery |
| Cocaine | broad orange band against the periphery |
| Heroin/Morphine Glucorinide | inner blue ring or broader blue band to the periphery |
| Marijuana/THC | inner thin charcoal ring |
| Methadone | broad deep purple band against the periphery |
| Percodan | broad tan band against the periphery |

I have found the sensitivity of the papers to coincide with thin layer chromatography results. It should be evident to one skilled in the art that greater sensitivity can be achieved by either molecular concentration techniques or extraction of urinary alkaloids and elution via ion exchange resins.

As indicated above, this invention has special utility in the detection of abuse type drugs in urine revealing visually, in a short interval, not only the fact that such a drug is present, but also identifying the particular drug involved. Additionally, test papers of this invention will immediately expose a user's attempt to defeat the test by substituting water for urine specimen. Further, the art is hereby afforded a wide variety of choices of formulations as well as preferred embodiments of this invention incorporating special constituents for particular purposes as impregnants of celluosic papers of strength and thickness facilitating drug detection use to best advantage.

The concept of using parahydroxybenzoic acid esters, preferably the methyl or propyl esters, is an important feature of this invention for the reason that it solves the problem of urine preservation without interfering with the test purpose or diminishing the utility or sensitivity of the present novel test papers in such application.

What is claimed is:

1. A method of producing a test paper useful in detecting the presence of abuse-type drugs in physiological fluid which comprises the steps of providing a first solution composed of bismuth subnitrate and acetic acid and water, providing a second solution composed of potassium iodide and a platinum salt and dilute hydrochloric acid, providing a third solution composed of potassium iodide in proportion about 50% greater than the potassium iodide in the second solution and a platinum salt in proportion about one-quarter that of the platinum salt in said second solution and dilute hydrochloric acid, admixing a part by volume of the first solution and 10 parts by volume of the second solution to provide a first combination solution, admixing another part by volume of the first solution with an equal part by volume of the third solution to provide a second combination solution, coating a portion of a bibulous paper strip with said first combination solution, drying the coated paper strip at about 30° C., then coating the dried coated paper strip with the second combination solution, and finally drying the overcoated bibulous paper strip at about 50° C. in high humidity.

2. The method of claim 1 wherein the first solution contains about 1.4 parts by weight of the bismuth subnitrate and about 14 parts by weight of the acetic acid and about 86 parts by weight of water, the second solution contains about 4.05 parts by weight of the potassium iodide and about 0.45 part by weight of the platinum salt and about 100 parts by weight of 2N hydrochloric acid and about 100 parts by weight of water, and the third solution contains about six parts by weight of the potassium iodide and about one-eighth part by weight of the platinum salt and about 100 parts by weight of the platinum salt and about 100 parts by weight of 2N hydrochloric acid and about 100 parts by weight of water, wherein the coated paper strip is dried at about 30° C. for about 3 hours, wherein the dried coated paper strip is cured for two weeks, and wherein the overcoated bibulous paper strip is dried at about 50° C. in high humidity until it is dry.

3. The method of making a test paper useful in detecting the presence of abuse-type drugs in physiological fluid which comprises the steps of contacting a bibulous cellulosic carrier of thickness from about 0.35 mm to about 0.45 mm and a dry weight of about 185 g per $M^2$ with a dilute hydrochloric acid solution of a platinum salt and an iodine salt, and thereafter drying the bibulous cellulosic carrier in static air at about 30° C.

4. The method of claim 3 in which the iodine salt is potassium iodide and the platinum salt is selected from the group consisting of $K_2PtCl_4$, $K_2PtCl_6$, $H_2PtCl_6$, $PtCl_3$ and $PtCl_4$.

5. A method for producing a test paper useful in detecting the presence of abuse-type drugs except cocaine in urine which comprises the steps of immersing bibulous paper sheet in dilute hydrochloric acid solution of iodochloroplatinate at about 20°–40° C., providing a second solution composed of about equal proportions of bismuth subnitrate and iodochloroplatinate and containing dilute hydrochloric acid and acetic acid, thereafter immersing the resulting coated sheet in the second solution, then drying the sheet at about 50° in high humidity.

* * * * *